United States Patent [19]

Mulshine et al.

[11] Patent Number: 4,569,788

[45] Date of Patent: Feb. 11, 1986

[54] MONOCLONAL ANTIBODIES AGAINST NON SMALL CELL LUNG CANCER

[75] Inventors: James L. Mulshine, Kensington; John D. Minna, Bethesda, both of Md.

[73] Assignee: The United States of America as represented by the Department of Health and Human Services, Washington, D.C.

[21] Appl. No.: 495,725

[22] Filed: May 18, 1983

[51] Int. Cl.⁴ .................. C12N 15/00; G01N 33/54
[52] U.S. Cl. ................. 260/112 R; 436/513; 436/548; 436/804; 436/808; 436/813; 435/4; 435/7; 435/29; 435/68; 435/172.2; 435/810; 435/948; 935/110
[58] Field of Search ............ 436/518, 536, 547, 548, 436/804, 808, 813, 513; 435/68, 70, 172, 240, 948, 4, 7, 29, 810; 260/112 R; 424/1.1, 9, 85, 88, 177; 935/110

[56] References Cited

U.S. PATENT DOCUMENTS

| | | | |
|---|---|---|---|
| 4,172,124 | 10/1979 | Koprowski et al. | 424/85 |
| 4,317,877 | 3/1982 | Balis et al. | 435/4 |
| 4,331,647 | 5/1982 | Goldenberg | 424/1.1 |
| 4,349,528 | 9/1982 | Koprowski et al. | 424/1.1 |
| 4,361,544 | 11/1982 | Goldenberg | 424/9 |

OTHER PUBLICATIONS

Mulshine, J. L. et al, J. of Immunology, vol. 131 (1), pp. 497–502 (7–1983).
Gazdar, A. F. et al, Seminars in Oncology, vol. 10 (1), pp. 3–19 (3–1983).
Carney, D. N. et al, Pathobiol Annual, vol. 12, pp. 115–136 (1982).
Baylin, S. B. et al, Proc. Natl. Acad, Sci, USA, vol. 79, pp. 4650–4654 (8–1982).
Cuttitta et al; PNAS, vol. 78, pp. 4591–4595 (1981).
Kohler et al; Nature, vol. 256, pp. 495–497 (1975).
Moody, T. W. et al, Science, vol. 214, pp. 1246–1248 (12–1981).
Brown, J. P. et al, Clinical Chemistry, vol. 27, pp. 1592–1595 (1981).
Minna et al, In Vitro, vol. 17, pp. 1058–1070 (1981).

Primary Examiner—Christine M. Nucker
Assistant Examiner—M. Moskowitz
Attorney, Agent, or Firm—John S. Roberts, Jr.

[57] ABSTRACT

Monoclonal antibodies 703D4 and 704A1 detect human non-small cell lung cancer (non-SCLC) and distinguish non-SCLC from all other types of lung cancer and normal tissue cells. These two antibodies may be utilized in kit form to distinguish non-SCLC from other forms of lung cancer. These monoclonal antibodies bind to $S^{35}$ methionine-incorporating protein doublets under reduced and unreduced conditions. The determinants bound by these antibodies on the 31 kiladalton protein are independent of each other as determined in radiolabelled competition assays.

6 Claims, 3 Drawing Figures

MONOCLONAL ANTIBODIES AGAINST NON SMALL CELL LUNG CANCER

DESCRIPTION OF THE MONOCLONAL ANTIBODIES

The monoclonal antibodies of this invention, 703D4 and 704A1, show significant binding activity with non-small cell lung cancers (non-SCLC). Neither MAB binds with small cell lung cancer or with normal lung tissue. Both antibodies precipitate 31 kilodalton doublet bands of [$^{35}$S] methionine-labelled proteins from human non-small cell lung cancer and human melanoma cells. Other binding characteristics are shown in Tables I-V.

Monoclonal antibodies 703D4 and 704A1 are two independent IgG$_{2A}$k antibodies that recognize different epitopes on the same 31K dalton protein or separate 31K dalton proteins. The distribution of these antigens is restricted to non-small cell forms of lung cancer. None of the SCLC tested have expressed these antigens, but some other non-pulmonary neoplasms, especially melanoma, express these epitopes. These antigens are not detected in normal adult human tissues by immunohistochemical or by radiobinding assays. The value of these antibodies is as members of panels of monoclonal antibodies used to distinguish non-small cell from small cell forms of lung cancer.

UTILITY

The monoclonal antibodies of this invention are useful in the detection and differentiation of human non-small cell lung cancer. The major histologic types of lung cancer are divided into two groups; squamous cell adenocarcinoma and large cell are collectively referred to as non-small cell lung carcinomas (nonSCLC). They are distinguished from small cell lung cancer (SCLC) by clinical presentation, response to chemotherapy and radiation therapy, and by biological characteristics. SCLC is very rarely localized, so that surgery or radiation therapy should not be used as the sole treatment; non-SCLC is much more amenable to local therapies. For example, over 90% of patients with SCLC respond to combination chemotherapy, while only 30-40% on non-SCLC patients respond. The ability to distinguish between non-SCLC and SCLC is crucial because major treatment decisions are based on the initial distinction between SCLC and non-SCLC.

In addition, these monoclonal antibodies (MAB) are specific for an antigenic phenotype found on non-SCLC and not found on normal cells, so these MABs function as a diagnostic reagent.

MATERIAL INFORMATION DISCLOSURE

Figure 1:
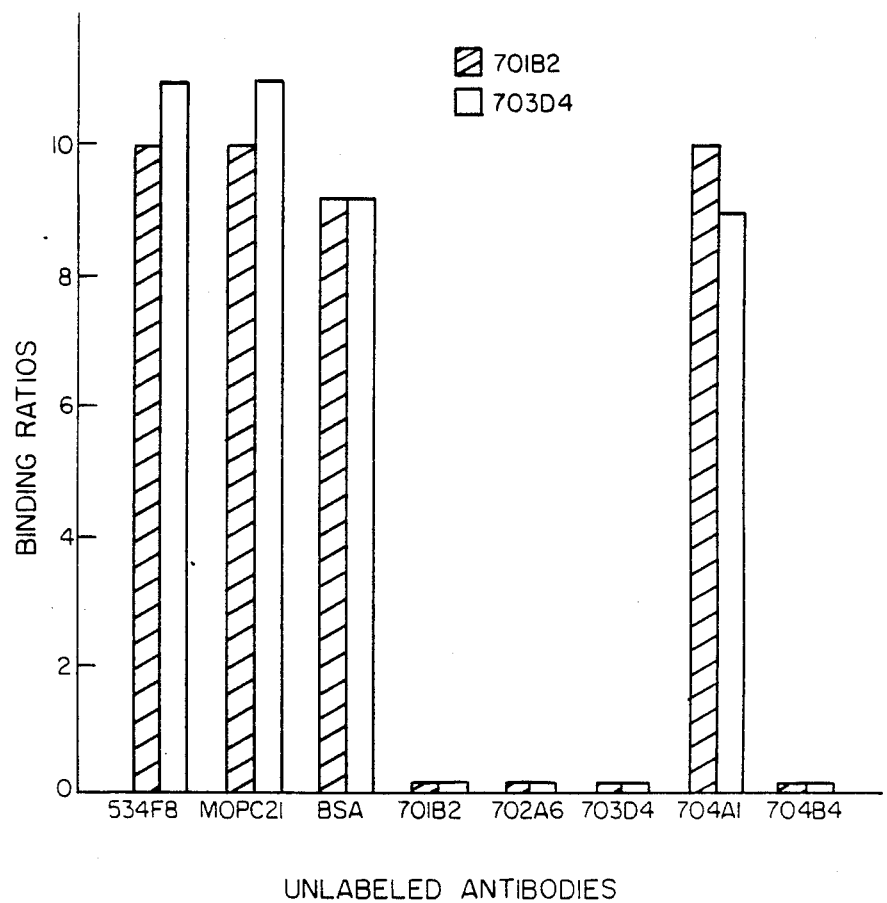
FIG. 1 is the competition binding study in which two radiolabelled antibodies compete with eight unlabelled antibodies or controls. Five hybridoma clones are used (701B2, 702A6, 703D4, 704A1, and 704B4). 534F8, MOPC21, and BSA (bovine serum albumin) are all controls. The binding ratios of two $^{125}$I labelled monoclonals, 701B2 and 703D4, shown when incubated with saturating concentrations of unlabelled antibodies. This test helps to distinguish the binding characteristics of a monoclonal antibody.

Bayline, Stephen B., et al, P.N.A.S., Vol. 79, p. 4650 (1982) teaches the discovery of the surface protein phenotypes that distinguish non-small cell from small cell lung cancers.

Brown, J. P. et al, Clinical Chemistry, Vol. 27, p 1592 (1981), teaches the use of monoclonal antibodies in specifying normal cells versus neoplastic cells. Although this article does disclose a means of differentiating lung cancer from normal cells, it lacks a means of diagnosing or differentiating between several types of lung cancer.

Minna, J. D., et al, In Vitro, Vol. 17, p 1058 (1981) and Cuttitta, F., et al, PNAS, Vol. 78, p 4591 (1981) both teach the production and the use of monoclonal antibodies specific for lung cancer, but these articles are limited to small cell lung cancer and do not disclose a means of differentiating small cell from non-small cell lung cancer.

Kohler, G. and Milstein, C., Nature, Vol. 256, p. 495 (1975) provides the premier disclosure of the monoclonal antibody technology, a modification of which was used in this invention.

STATEMENT OF DEPOSIT

Monoclonal antibodies, 703D4 and 704A1, have been deposited in the American Type Culture Collection 12301 Parklawn Drive, Rockville, MD, 20852. The ascession numbers are HB 8301 and HB 8302, respectively.

BACKGROUND

Four types of lung cancer are found in man: squamous, adeno, small cell, and large cell. Each tumor expresses specific differentiation features or surface phenotype determinants, all of which distinguish these cells from normal cells. The development of monoclonal antibody diagnostic techniques has greatly enhanced the production of reagents capable of differentiating normal cells from cancer cells and differentiating types of cancer cells from other cancer cells. The present invention discloses a method and the monoclonal antibodies capable of specifying non-small cell lung cancer from other types of lung cancer and from normal lung tissue.

The development of somatic cell hybrid technology for the production of monoclonal antibodies has produced several monoclonal antibodies with various degrees of specificity for a variety of human cancers.

The present invention discloses the use of this technology to prepare antibodies that not only detect human lung cancer but also differentiate between the varieties of human lung cancer.

The antibodies (MAB) of this invention detect different epitopes on 31 kilodalton [$^{35}$S] methionine incorporating proteins. Radiobinding and immunohistochemical studies show that these MABs bind to most (11/13) human non-small cell lung cancer (adenocarcinoma, epidermoid, and large cell) but do not bind to small cell lung cancer. Currently, this distinction is made by light microscopy. However, even expert lung cancer pathologists disagree on this subtyping of lung cancer. We have found that SCLC contains a cytogenetic marker, the deletion on the short arm of chromosome 3, elaborate peptide hormones such as bombesin, and have high specific activity of neuron-specific enolase, L-dopa decarboxylase, and creatine phosphokinase BB. These markers are either absent or expressed at much lower levels in non-SCLC. In addition, SCLS and non-SCLC have distinctly different membrane protein phenotypes by two-dimensional gel electrophoresis.

SPECIFIC DISCLOSURE

The monoclonal antibodies of this invention were produced by generally following a variation of the procedure outlined in Koprowski, U.S. Pat. Nos. 4,172,124 and 4,196,265. This variation permits the production of monoclonal antibodies suitable for the detection and/or diagnosis of non-small cell lung cancer. In general, antibody forming cells are removed from the spleen of immunized mice and mixed with mouse myeloma cells. Some of these cells fuse into hybrids, the selection of which occurs by placing the mixture in HAT medium (i.e., only hybrid cells survive). Those hybrids that produce antibody are then cloned and used to produce large amounts of antibody. The specific process used in the present invention follows.

The cell line used for immunization (NCI-H157) was derived from a malignant pleural effusion of an untreated patient with large cell lung cancer. At the time of immunization, the cell line had been maintained in culture for 24 months.

Small cell-large cell variants are easily confused with non-SCLC. These clinically important transformants are distinctive in having reduced or absent levels of L-dopa decarboxylase while retaining elevated levels of neuron-specific enolase and the 3p chromosomal deletion. Human SCLC cultures that converted to large cell cytology including one line from a patient whose tumor had mixtures of SCLC and large cell histology (line NCI-H82) while another occurred spontaneously during long-term tissue culture (line NCI-N231/417) were used as paradyms for this phenomenon.

Spleen cells from a BALB/c mouse hyperimmunized with NCI-H157 cells ($10^7$ live cells initially delivered subcutaneously with complete Freund's adjuvant, then repeated weekly four times intraperitoneally, and finally intravenously 72 hours prior to fusion) were fused with the mouse myeloma cell line X63-Ag8.653. After 10 days, microtiter wells positive for growth were tested for antibody binding activity. In the preliminary screen using a solid phase RIA to test for binding of antibody in culture supernatants to gluteraldehyde-fixed human cell lines, wells were selected with antibodies which bound to NCI-H157 (non-SCLC), but not NCI-H128 (qSCLC) or NCI-H128BL (human B-lymphoblastoid cell line autologous to NCI-H128). Those hybridomas that proved to be stable through five miniclonings followed by strict single cell cloning, while maintaining specific binding for NCI-H157 but not to SCLC lines or B-lymphocyte lines, were introduced into BALB/c mice for ascites production.

IMMUNOASSAYS

Rabbit anti-mouse immunoglubulin (RAM:Miles Laboratories, Inc., Elkhart, IN) directed against the mouse immunoglobulin $Fab_2$ region was used in solid phase RIA systems. One modification of this system was the omission of secondary antibody in certain assays utilizing staphylococcal Protein A (Pharmacia, Piscataway, NJ) directly binding primary antibody. The monoclonal antibodies were class typed after binding to fixed cells by using a modification of the enzyme-linked immunoabsorbent assay, with rabbit anti-mouse immunoglobulin class-specific reagents, followed by detection of the bound rabbit antibody with horseradish peroxidase-labeled goat and anti-rabbit IgG (all detector reagents diluted 1:500).

For direct assays, $NH_4SO_4$ purified monoclonal antibodies were labeled with $^{125}I$ using the chloramine-T method with 20 μg of monoclonal antibody labeled to specific activities of 1–2 μCi/ug. Labeled antibodies were then titered on 96 well plates of solid phased NCI-H157 cells. Direct assays of solid phase cells and membranes from normal tissue obtained at autopsy were preformed by incubating plates of glutaraldehyde-fixed targets with the $^{125}I$ labeled monoclonal antibodies (50 ng, 100,000 cpm/0.025 ml/well) for 1 hr. in PBS/1% BSA and then washing the plates seven times with PBS. For competition studies the labeled antibodies in a total volume of 0.05 ml were then co-incubated with cold antibodies (5 μg) to determine competition in binding to solid phase NCI-H157 cells.

IMMUNOPRECIPITATIONS

Human tumor cells were incubated overnight with [$^{35}$S] methionine (800 μCi/ml, Amersham Corp., Arlington Heights, IL) in methionine free medium (GIBCO, Grand Island, NY). Cell lysates were prepared and preincubated with linking antibody horse anti-mouse IgG (Miles Laboratories, Inc., Elkhart, IN) bound to staphylococcal protein A (Pansorbin, Calbiochem-Behring Corp., La Jolla, CA). Aliquots of $10^6$ cpm of cell lysates were first incubated with ammonium sulfate purified ascitic protein and then with horse anti-mouse IgG bound to protein A. The protein A complex was sedimented and washed five times and the antigens were analyzed along with both low and high molecular weight pre-labeled markers (Bethesda Research Laboratories, Gaithersburg, MD) by 12% SDS-PAGE in both reduced and unreduced conditions.

IMMUNOHISTOCHEMISTRY

Normal and malignant human tissue as well as nude mouse xenotransplanted tumors were obtained, formalin-fixed, embedded, cut, and stained using the mehtod of Hsu et al, *J. Histochem. Cytochem.*, Vol. 30, p. 1079 (1982). Ammonium sulfate purified ascites was standardized to 10 μg of protein/ml concentration for use in the immunohistochemistry assays.

Primary antibodies were incubated for one hour at room temperature in a humidity chamber. Biotinylated secondary antibody and avidin-biotin conjugated horseradish peroxidase were obtained from Avidin-Biotin-Complex (ABC) kits (Vector Laboratories, Burlingame, CA). Both incubation of the antibody and of ABC were for 30 minutes at room temperature. The enzyme substrate was nickel chloride impregnated with diaminobenzidine which was incubated for 20 minutes.

RESULTS

Generation of Antibodies

Figure 2:
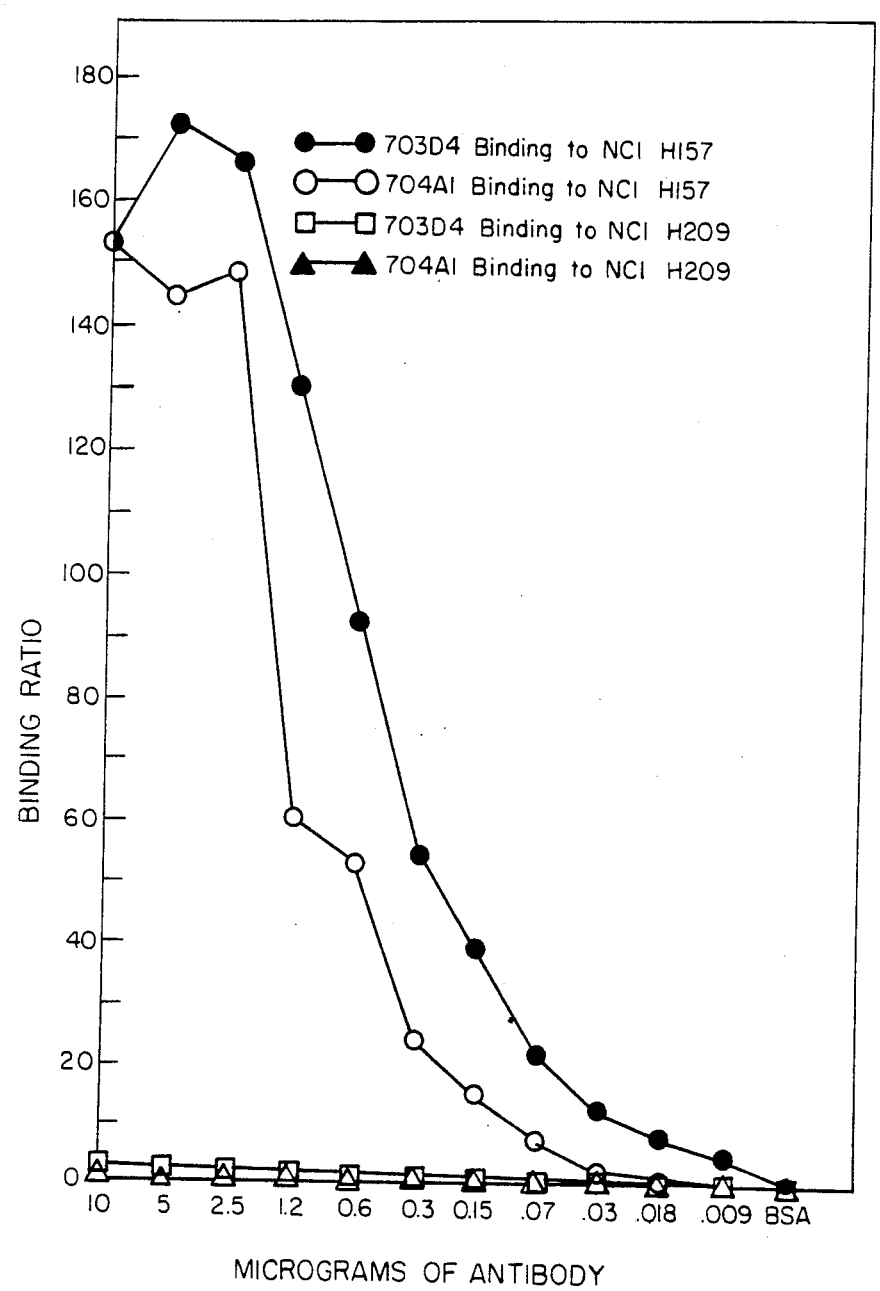
FIG. 2 is the titration binding curve of monoclonal antibodies 703D4 and 704A1 with solid phase NCI-H157 cells (original immunizing large cell cancer cell line) and NCI-H209 cells (human SCLC line) in a direct radioassay at serial two-fold dilutions with results expressed as binding ratios. This assay establishes the titer or potency of an antibody preparation.

After fusion, 169 of the 672 wells showed growing hybrids, and 38 wells showed selective binding to the human large cell lung cancer line (NCI-H157) but not to human SCLC (NCI-H128, NCI-H209) or B-lymphoblastoid (NCI-H128BL, NCI-H209BL) lines. Following sequential mini-cloning, five of the original selective clones were established as stable, hybridoma lines. The five cloned lines were all found to secrete IgG$_{2A}$k. All five clones were introduced into BALB/c mice for ascites production. Purified antibodies were subsequently labeled with $^{125}$I and used in competition studies—four of the five clones competed for the same epitope, while one (704A1) detected a different epitope (FIG. 1). For this reason, for all subsequent characterization studies, only two antibodies (704A1 and 703D4) recognizing different epitopes were used. In screening cell lines in solid phase RIA assays, both a double antibody system and direct Staph Protein A binding were used with similar results. FIG. 2 shows a direct Staph Protein A binding titration curve of the two monoclonal antibodies with the human large cell lung cancer (NCI-H157) which was the immunogen line. The monoclonal antibodies fail to bind significantly to the SCLC line (NCI-H209) as shown in FIG. 2.

Reaction of anti-large cel monoclonal antibodies with various cell lines in solid phase RIA assay The two monoclonal antibodies were tested for binding to a panel of malignant and nonmalignant human cell lines as well as rodent cell lines shown in Tables I–III. Monoclonal antibody 703D4 showed significant binding to 9 to 11 of the non-SCLC lines, including two mesothelioma cell lines, while 704A1 only bound to 5 of the non-SCLC; neither of the antibodies showed significant binding to any of the 9 SCLC lines or to the two small cell lines that had converted to large cell histologic variants (NCI-H82 and NCI-N231/417).

All different cell types of non-SCLC were bound by either one or the other of the monoclonal antibodies. 703D4 bound both of the human large cell tumor lines (9812 and NCI-H157). Extensive reactivity with human melanoma cell lines was also found. Of the eight melanoma lines tested, seven were positive for binding in all but one case with both of the monoclonal antibodies. Two other human tumor lines, a renal carcinoma and osteogenic sarcoma, also expressed the antigen(s) bound by these antibodies. The remaining nine human tumor cell lines tested representing 6 different malignancies, including myeloma, T-cell leukemia/lymphoma, neuroblastoma, breast cancer, colon cancer, and one melanoma failed to express detectable levels of these antigens (Table II). Low magnitude, but consistent, binding was found with both antibodies to the fetal lung fibroblast line IMR-90 but not to the fetal lung fibroblast line HR-6. A variety of rodent cell lines failed to exhibit detectable expression of these determinants as measured in the solid phase radioimmunoassay (Table III).

Immunoprecipitation results

Figure 3:
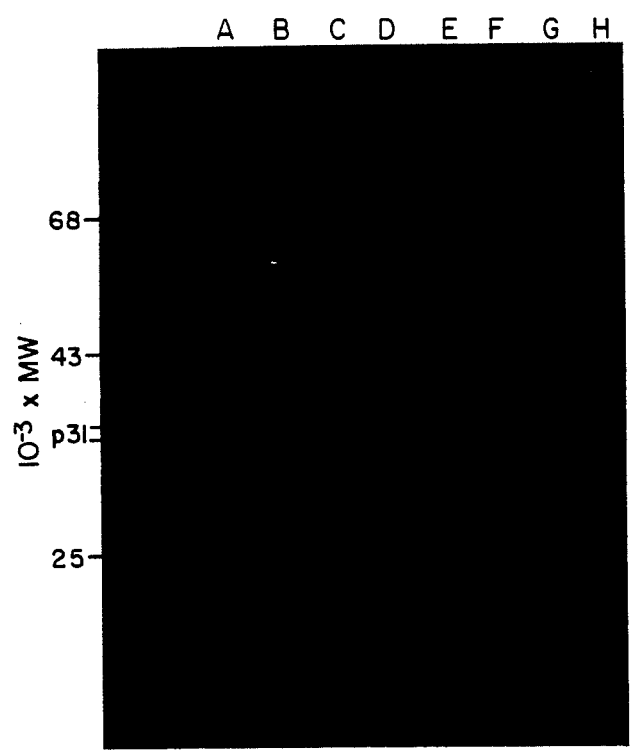
FIG. 3 is the SDS-page analysis of antigens immunoprecipitated by MABs 703D4 and 704A1 from metabolically labelled cellular lysates of human large cell lung cancer cells (NCI-H157) and human melanoma cells (NCI-H234); immunoprecipitation of [$^{35}$S] methionine incorporating NCI-H157 cell lysates (Lane A), precipitation with monoclonal antibody 703D4 (Lane B), precipitation with monoclonal antibody 704A1 (Lane C) and precipitation with control murine IgG MOPC 21 (Lane D); immunoprecipitation of [$^{35}$S] methionine incorporating NCI-H234 cell lysates (Lane E), precipitation with monoclonal antibody 703D4 (Lane F), precipitation with monoclonal antibody 704A1 (Lane G), and precipitation with control murine IgG MOPC21 (Lane H). Note the doublet at 31 kilodaltons in Lane C. This analysis helps establish the biochemical profile of the antibody target.

Immunoprecipitation studies of monoclonal antibodies 703D4 and 704A1 were performed with biosynthetically labeled NCI-H157 cell lysates as well as NCI-H234, a melanoma line (FIG. 3). The protein(s) bearing the antigenic determinant recognized by these antibodies appear to be of identical molecular weight of 31 kilodalton (p31) in both unreduced and reduced conditions. Monoclonal antibody 703D4 precipitates a protein which is doublet in nature and no appreciable band is specifically immunoprecipitated using the B-lymphoblastoid line lysate. Monoclonal antibody 704A1 precipitates a very similar but not identical doublet protein, despite identical lysates and antibody concentrations. Both antibodies precipitate the 31 kilodalton doublet bands from membrane proteins of [$^{35}$S] methionine-labeled melanoma cell NCI-H234. Neither antibodies precipitate any protein from cell lysates labeled with [$^{35}$S] methionine from SCLC line NCI-H128.

Immunohistochemistry testing of tumors

Nude mouse heterotransplants of various human lung cancer lines were screened with both 703D4 and 704A1 using concentrations of 10 µg/ml of ammonium sulfate purified antibodies. Results of staining of paraffin-embedded, formalin-fixed tissues are shown in Tables IV and V. The antigen recognized by 704A1 is expressed in a diffuse stippled pattern in the cytoplasm and also extracellularly in keratinized areas. Antibody 703D4 stained four of the six non-SCLC lines as did 704A1. Antibody 703D4 was negative with adenocarcinoma A549 and positive with squamous cell carcinoma NCI-H348 while the reverse was true with 704A1. Thus, the antigens were stable to the fixation and embedding procedures and at least some tumors can express one but not the other of the epitopes.

Tests of antibody binding to normal tissues

The direct immunoassay using iodinated monoclonal antibodies as a target solid phased membrane preparations (0.050 ml of a 1% v/v suspension/well) of 32 different normal adult tissues obtained at autopsy failed to show any significant binding of the antibodies to normal tissues. Since we were concerned that the antibodies could bind to rare subsets of normal cells, immunohistochemistry was performed. A screen of 9 normal adult human tissues (formalin-fixed, paraffin-embedded autopsy material) with both monoclonal antibodies failed to show significant binding (Table V).

The monoclonal antibodies of this invention are suitable for use in diagnostic kits consisting of antibodies 703D4 and 704A1, the oncogenic cells to be tested, and any suitable screening technique (such as immunoassay, immunoprecipitation assays, or immunohistochemistry assays). An outside source of target cells are added to the kit's ingredients. Said kit includes a source of antibody (at least one or both of 703D4 and 704A1) and the screening means for the assays shown above.

Tables I–V illustrate the binding attributes of monoclonal antibodies 703D4 and 704A1. Tables I and IV show binding to a variety of lung cancer cell lines. Significantly superior binding ratio to the non-small cell lung cancers is shown. Tables II and III illustrate the binding ability to a variety of non-lung cancers. Table V emphasizes the total lack of binding to normal human tissue cells.

TABLE I

Binding of Monoclonal Antibodies 703D4 and 704A1 to Human Lung Cancer Lines in Solid Phase Radioimmunoassay[a]

| Human Lung Cancer Lines | | Binding Ratio[b] 703D4 | 704A1 |
|---|---|---|---|
| Large Cell | NCI-H157 | 170 | 140 |
| | 9812[c] | 6 | <1 |
| Adenocarcinoma | NCI-H125 | 1 | 1 |
| | NCI-H23 | 201 | 3 |
| | A549 | 18 | 18 |
| | SK-LU-1 | 32 | 2 |
| | NCI-H324 | 2 | 3 |
| | Calu-6 | 6 | 1 |
| Mucoepidermoid | NCI-H292 | 7 | <1 |
| Mesothelioma | NCI-H28 | 17 | 9 |
| | NCI-H226 | 6 | 1 |
| Small Cell | NCI-H69 | 2 | <1 |
| | NCI-H187 | 1 | <1 |
| | NCI-H146 | 1 | 2 |
| | NCI-H60 | 1 | 1 |
| | NCI-H209 | 1 | 1 |
| | NCI-H249 | 2 | 2 |
| | NCI-N231 | <1 | <1 |
| | NCI-H128 | <1 | <1 |
| | NCI-H-123 | 1 | 2 |
| SCLC Converters[d] | NCI-N231/417 | 1 | 1 |
| | NCI-H82 | 1 | 2 |

[a]Assays were performed in quadruplicate using $^{125}$I-protein A assay with monoclonal antibodies from ascites purified with 40% ammonium sulfate and used at concentration of 1 ug/ml.
[b]Binding Ratio = (cpm test well - cpm negative control) : cpm negative control to allow comparison between assays. Results are the average of quadruplicate determinations (less than 20% variance between wells for any one test). The negative control (within the range of 50-300 cpm for all cell lines tested) was obtained by omitting the monoclonal antibody and substituting PBS in the reaction. A significant Binding Ratio is one higher than two.
[c]Tumor type of 9812 has been referred to as lung cancer and melanoma. Histologically, the nude mouse heterotransplant is a large cell undifferentiated tumor compatible with either type.
[d]Cell lines which in culture has undergone histologic conversion from small cell to large cell with loss of typical small cell APUD characteristics.

TABLE II

Nonpulmonary Human Tumor Cell Lines with Significant Binding Ratio in Solid Phase Radioimmunoassays with Monoclonal Antibodies 703D4 and 704A1

| Cell Line | Type | Binding Ratio 703D4 | 704A1 |
|---|---|---|---|
| Renal Cell Carcinoma | NCI-H201 | 23 | 30 |
| Osteogenic Sarcoma | NCI-H135 | 9 | 3 |
| | 6208-WE | 17 | 20 |
| Melanoma | A375 | 9 | 5 |
| | NCI-H234 | 4 | 4 |
| | A875 | 8 | 6 |
| | SKMEL-28 | 4 | 4 |
| | A3827 | 20 | 3 |
| | A101 | 14 | 2 |

TABLE III

Cell Lines With Low or Insignificant Binding of Anti-Human Large Cell Lung Cancer Monoclonal Antibodies 703D4 and 704A1 in Solid Phase Radioimmunoassay

| Target Cell | | Binding Ratio 703D4 | 704A1 |
|---|---|---|---|
| B-Lymphoblastoid | NCI-H128BL* | <1 | <1 |
| | NCI-H209BL* | <1 | <1 |
| Macrophage | U937 | 2 | 1 |
| Multiple Myeloma | U266 | <1 | <1 |
| T-cell Leukemia/ | Hut78 | 1 | 3 |
| Lymphoma | Hut102 | <1 | <1 |
| Neuroblastoma | CHP100 | <1 | 2 |
| | IMR-32 | 2 | <1 |
| Breast Cancer | MCF-7 | 1 | 1 |
| | MDA-MB231 | 2 | 1 |
| Melanoma | SKMEL-31 | 2 | 1 |
| Colon | SWI-222 | 3 | 3 |
| Fibroblasts, human | IMR-90 | 3 | 4 |
| | HR-6 | 2 | 2 |
| Rodent Cell Lines: | | | |
| Mouse RAG (BALB/c, renal cell carcinoma) | | 1 | 1 |
| B82 (C3H, transformed fibroblasts) | | <1 | <1 |
| L51784R (DBA, L cell) | | <1 | 2 |
| L cell (TH-)(mouse fibroblast) | | <1 | <1 |
| Rat GH$_3$ (pituitary tumor) | | <1 | <1 |
| PC12 (Pheochromocytoma) | | 1 | 1 |
| Chinese Hamster E36 (transformed lung) | | 2 | 2 |

*B-Lymphoid line derived from SCLC patient.

TABLE IV

Binding of Nude Mouse Tumor of Human Lung Cancer Cell Lines Heterotransplants in Immunohistochemical Assay With Monoclonal Antibodies 703D4 and 704A1

| | Staining 703D4 | 704A1 |
|---|---|---|
| Non-Small Cell Carcinoma of Lung | | |
| NCI-H23 (Adenocarcinoma) | + | + |
| NCI-H207 (Adenocarcinoma) | + | + |
| NCI-H292 (Mucoepidermoid) | + | + |
| A549 (Adenocarcinoma) | − | + |
| NCI-H348 (Squamous Cell) | + | − |
| NCI-H125 (Adenocarcinoma) | − | − |
| Small Cell Lung Cancer | | |
| NCI-N179 | − | − |
| NCI-H69 | − | − |
| NCI-H128 | − | − |
| NCI-H328 | − | − |
| NCI-H329 | − | − |
| Small Cell to Large Cell Converters | | |
| NCI-N231/417 | − | − |
| NCI-H82 | − | − |

TABLE V

Binding of Anti Large Cell Monoclonal Antibodies 703D4 and 704A1 with Normal Human Tissues in Immunohistochemical Assay

| Normal Tissue | 703D4 # Positive/Total | 704A1 # Positive/Total |
|---|---|---|
| Lung | 0/5 | 0/5 |
| Liver | 0/3 | 0/3 |
| Kidney | 0/3 | 0/3 |
| Brain | 0/4 | 0/4 |
| Pancreas | 0/2 | 0/2 |
| Prostate | 0/2 | 0/2 |
| Bladder | 0/2 | 0/2 |
| Skeletal Muscle | 0/1 | 0/1 |
| Colon | 0/1 | 0/1 |

We claim:

1. IgG2Ak monoclonal antibody designated 704D4 having the essential characteristics of ATCC No. HB8301, said characteristics include binding to human non-small cell lung cancer.

2. IgG2Ak monoclonal antibody designated 704A1 having the essential characteristics of ATCC No. HB8302, said characteristics include binding to human non-small cell lung cancer.

3. Monoclonal antibodies 703D4 and 704A1, each specific for non-small cell lung cancer, that specifically bind to $^{35}S$ methionine-incorporating 31 kilodalton protein, said protein derived from lysates of human tumor cells, and said protein containing determinants that are independent of each other as established by radiolabelled competition assays.

4. An immunoassay for the detection of human non-small cell lung cancer comprising
producing monoclonal antibodies 703D4 and 704A1;
combining one or both antibodies with a sample of human lung cancer cells;
assaying for antibody binding to human non-small cell lung cancer.

5. An immunoassay for the detection of human non-small cell lung cancer consisting essentially of
producing monoclonal antibodies 703D4 and 704A1;
said monoclonal antibodies being capable of binding to adenocarcinoma, epidermoid carcinoma, large cell carcinoma, or mesothelioma human non-small cell lung cancers;
said monoclonal antibodies differentiate between human non-small cell lung cancer and any of the group of cancers selected from small cell lung cancer, multiple myeloma, T-cell leukemia, and neuroblastoma;
combining one or both antibodies with a sample or human lung cancer cells;
assaying for antibody binding to human non-small cell lung cancer.

6. A diagnostic kit suitable for detecting and diagnosing human non-SCLC to be used with a source of monoclonal antibodies consisting essentially of either or both monoclonal antibodies 703D4 and 704A1; a means of detection selected from the group consisting of a radioisotopic label, a chromophore, and an enzyme label;
the above elements of the kit to be used in conjunction with an outside source of target cells for testing of oncogenic properties, said kit including container means for said monoclonal antibodies, plate or slide means for combining said target cells with said monoclonal antibodies, and a packaging means for combining said container means, said plate or slide means, and said means of detection.

* * * * *

UNITED STATES PATENT OFFICE
CERTIFICATE OF CORRECTION

Patent No. 4,569,788     Dated February 11, 1986

Inventor(s) James L. Mulshine, John D. Minna

It is certified that error appears in the above-identified patent and that said Letters Patent are hereby corrected as shown below:

Claim 1, line 1 --

"704D4" should be --703D4--.

Signed and Sealed this

Twenty-ninth Day of July 1986

[SEAL]

Attest:

Attesting Officer

DONALD J. QUIGG

Commissioner of Patents and Trademarks